United States Patent [19]
Tabata et al.

[11] Patent Number: 5,200,175
[45] Date of Patent: Apr. 6, 1993

[54] HAIR TREATMENT COMPOSITION

[75] Inventors: Yoshiko Tabata, Chiba; Naohisa Kure, Tokyo, both of Japan

[73] Assignee: Kao Corporation, Tokyo, Japan

[21] Appl. No.: 798,648

[22] Filed: Nov. 26, 1991

[30] Foreign Application Priority Data

Nov. 28, 1990 [JP] Japan .................. 2-328288

[51] Int. Cl.$^5$ .................. A61K 7/09; A61K 7/13
[52] U.S. Cl. ............................ 424/70; 424/72
[58] Field of Search ............ 424/70, 72; 435/113, 435/72, 61

[56] References Cited

U.S. PATENT DOCUMENTS

| | | | |
|---|---|---|---|
| 4,272,517 | 6/1981 | Yoneda et al. | 424/72 |
| 4,919,920 | 4/1990 | Devos | 424/61 |
| 4,947,878 | 8/1990 | Crews et al. | 424/71 |
| 4,961,925 | 10/1990 | Tsujino et al. | 424/72 |

FOREIGN PATENT DOCUMENTS

| | | |
|---|---|---|
| 0302265 | 2/1989 | European Pat. Off. . |
| 0320612 | 6/1989 | European Pat. Off. . |
| 3022049 | 12/1981 | Fed. Rep. of Germany . |
| 2348695 | 11/1977 | France . |

Primary Examiner—Thurman K. Page
Assistant Examiner—D. Colucci
Attorney, Agent, or Firm—Oblon, Spivak, McClelland, Maier & Neustadt

[57] ABSTRACT

A hair treatment composition Which comprises (A) 3 to 10% by weight, calculated as cysteine, of cysteine or its salt, (B) a saccharide or a polyhydric alcohol which has 4 to 20 carbon atoms, has 3 or more hydroxyl groups in the molecule, and which has no aldehyde group or ketone group, with the proportion by weight, (B)/(A) being less than 3.

6 Claims, No Drawings

HAIR TREATMENT COMPOSITION

BACKGROUND OF THE INVENTION

1. Field of the Invention:

This invention relates to a hair treatment composition and more particularly to a hair treatment composition comprising cysteine or a salt thereof, which is capable of preventing flaking of the hair (recrystallization of the composition onto the hair fibres) and is mild to the skin.

2. Description of the Background

Cysteine and its salts possess mild reductivity and are widely used as a component of permanent wave agents, styling agents and so on.

Because of the weak reductivity of cysteine compared to thioglycolic acid, a permanent wave agent containing cysteine is generally used in such manner that the hair is first pretreated with the agent and then wound on a rod by fingers. This means that professional hair dressers' fingers undergo prolonged time of contact with the agent, which causes irritation to the skin of the fingers.

Cysteine is known to have weak reductivity. In order to supplement this weak reductivity, heat is often applied to the hair after treated with a permanent wave first agent containing cysteine. However, it sometimes causes irritation to the scalp.

It has also been noted that cystine, which is formed by oxidation of cysteine, is sparingly soluble and causes "flaking" which is a phenomenon where white crystals are deposited on the hair or on the skin of the fingers. Flaking should desirably be avoided because it brings about unattractive appearance, is rough and imparts a frictional feeling to the touch of the hair and chapped hands or fingers of professional hairdressers.

In order to overcome the flaking, several methods have been proposed, which include a method where a cysteine having racemic structure is used (Jpn. Kokai SHO 56-139411) and a method where N-acyl-cysteine or N-acyl-cystine is used (Jpn. Kokai SHO 52-128241 and 53-72835). These methods, however, result in insufficient waving, or waves, formed by these methods, lack elasticity when compared to those formed by the use of cysteine itself. Another method employs alkanediol added to cysteine (Jpn. Kokai HEI 2-502539). This method is accompanied by the drawback in that a sufficient effect can only be obtained when 300% or more of alkanediol based on cysteine is used, which leads to a restricted formulation of a composition.

Accordingly, development of a hair treatment composition which causes no flaking, is mild to the skin with the inherent activity of cysteine being maintained is still desired.

SUMMARY OF THE INVENTION

Accordingly, one object of the present invention is to provide a hair treatment composition which is mild to the skin and which prevents flaking (recrystallization of the composition).

Briefly, this object and other objects of the present invention as hereinafter will become more readily apparent can be attained by a hair treatment composition which comprises (A) 3 to 10% by weight, calculated as cysteine, of cysteine or its salt, and (B) a saccharide or a polyhydric alcohol which has 4 to 20 carbon atoms, has 3 or more hydroxyl groups in the molecule, and has no aldehyde group or ketone group, with the proportion by weight of (B)/(A) being less than 3.

DETAILED DESCRIPTION OF THE PREFERRED EMBODIMENTS

The discovery of the present invention is that when a small amount of a specific saccharide or a polyhydric alcohol is added to cysteine, the effectiveness of cysteine is maintained, and flaking and irritation to the skin are avoided.

Examples of Component (A) of the present composition include L-cysteine and the hydrochloride of L-cysteine. This compound or its salt is incorporated into a hair treatment composition in an amount of 3 to 10% by weight calculated as cysteine. If component (A) is present in amounts less than 3%, the required reductivity cannot be obtained, while amounts in excess of 10% by weight are not preferable in view of the stability of the component system.

Component (B), which is a saccharide or polyhydric alcohol having 4 to 20 carbon atoms, should have 3 or more hydroxyl groups in the molecule and should have no aldehyde group or a ketone group in the molecule. If a compound having less than 3 hydroxyl groups in the molecule is used, sufficient effects cannot be obtained in terms of both mildness to the skin and prevention of flaking. A compound having an aldehyde group or a ketone group is not preferred, because it reacts with the amino group or mercapto group present in the molecule of cysteine.

Examples of component (B) of the composition include monosaccharides having 4 to 10 carbon atoms and having no aldehyde or ketone group; $C_4$–$C_{10}$ straight chain or cyclic polyhydric alcohols; condensation products of 2 or 3 of these monosaccharides or polyhydric alcohols; saccharides which are produced by condensation of 2 or 3 monosaccharides having 4 to 10 carbon atoms and also having an aldehyde group or a ketone group, with the aldehyde group or ketone group being eliminated in the course of the condensation process.

In more detail, examples of component (B) include (1) aldonic acids such as gluconic acid; 2) saccharic acids such as glucosaccharic acid; (3) sugar alcohols such as sorbitol; (4) saccharides such as saccharose and trehalose, which are obtained by condensation of 2 or 3 members selected from the group consisting of aldonic acids such as gluconic acid, saccharic acids such as glucosaccharic acid, sugar-alcohols such as sorbitol, mannitol and xylitol, uronic acids such as glucuronic acid, amino sugars such as glucosamine and N-acetyl glucosamine, deoxysugars such as deoxyglucose, sugar ethers such as methylglucose, aldoses such as glucose and ketoses such as fructose; with free aldehyde or ketone groups being eliminated through the condensation process; (5) cyclic polyhydric alcohols such as inositol. Among them, sorbitol, mannitol, maltitol, xylitol, saccharose, gluconic acid or its salts and inositol are preferred. Preferred examples of the salts of glucuronic acid include alkali metal salts such as Na and K salts; alkaline earth metal salts such as Ca salts; $NH_4^+$ salts; primary, secondary and tertiary amine salts such as monoethanolamine, diethanolamine and triethanolamine salts; and quaternary ammonium salts. Among them, the most preferred are sodium salts, potassium salts, calcium salts, monoethanolamine salts and triethanolamine salts. A portion of hydroxyl groups of these saccharides and polyhdric alcohols may be substituted by a hydrogen, alkyl such as methyl, alkoxy such as methoxy, amino, carboxyl, acyloxy, acetamino, succinyloxy or the like groups, or may be esterified with sulfuric acid or phosphoric acid.

The proportion of component (B) in the hair treatment composition of this invention is less than 3 times by weight of component (A). Amounts in excess of more than 3 times by weight are not desired because of restrictions on the formulation. Preferred amounts of component (B) are 0.5 to 20% by weight based upon the total composition, with 2 to 10% by weight being particularly preferred.

The hair treatment composition of this invention may further contain other compatible ingredients which are generally used in this technical field so far as they do not impede the effects of the invention. Examples of such ingredients include various surfactants, solvents, humectants, sensation improvers, oils, antiseptics, colorants, perfumes, stabilizers, suspending agents, appearance controllers, viscosity modifiers, antiinflammatory agents, chelating agents, water, and so on.

The hair treatment composition of this invention is useful for formulating permanent wave agents, set lotions, pretreatment agents for hair dyes and the like. When used for formulating a permanent wave agent or a setting lotion, components (A) and (B) are preferably blended with a chelating agent such as ethylenediamine tetracetate and with a base such as an amine to adjust the pH to within the range of 7.0 to 10.0, with the composition being used in the form of an aqueous solution. Further, it is preferred that the hair treatment composition of the invention be used as a first liquid of a permanent wave agent.

Having now generally described this invention, a further understanding can be obtained by reference to certain specific examples which are provided herein for purposes of illustration only and are not intended to be limiting unless otherwise specified.

EXAMPLE 1

Permanent wave first liquids formulated as shown in Table 1 were prepared, and the effects of permanent waving, mildness to the skin and presence or absence of flaking were determined. The results are also shown in Table 1.

(1) Effect of permanent waving

Each of the permanent wave first liquids formulated as shown in Table 1 was used together with a commercially sold permanent wave second liquid for perming the hair of a subject, and the quality of waves or curls of the hair was observed by the naked eye.

(2) Flaking

Presence or absence of flaking was observed by the naked eye at the time of perming and determined according to the following criteria:

No flaking: AA
Slight flaking: A
Flaking is noticed: C
Considerable flaking: D (3) Mildness to the skin The compositions of Table 1 were applied to the skin of the inner part of the forearm of 10 test subjects 10 times continuously, and redness of the skin was determined according to the following criteria:

| | |
|---|---|
| Same degree of redness as comparative product was observed | X |
| Suppression of redness was clearly observed compared to comparative product | O |

TABLE 1

| | (% by weight) | | | | |
|---|---|---|---|---|---|
| | Invention products | | | | Comparative Product |
| Components | 1 | 2 | 3 | 4 | 5 |
| L-cysteine | 6.0 | 6.0 | 6.0 | 6.0 | 6.0 |
| Ammonium thioglycolate | 1.0 | 1.0 | 1.0 | 1.0 | 1.0 |
| EDTA.4Na | 0.5 | 0.5 | 0.5 | 0.5 | 0.5 |
| Monoethanolamine | ← Suitable amount*1 → | | | | |
| Inositol | 5.0 | — | — | — | — |
| Saccharose | — | 5.0 | — | — | — |
| Sodium gluconate | — | — | 5.0 | — | — |
| Sorbitol | — | — | — | 5.0 | — |
| Water | ← Balance → | | | | |
| Effect of permanent waving | Good | Good | Good | Good | Good |
| Flaking | A | AA | AA | A | C-D |
| Mildness to the skin | O | O | O | O | X |

*1 Amount required to adjust pH to 9.0

EXAMPLE 2

Using the compositions shown in Table 2, an accumulated stimulation test was conducted on a group of female white guinea pigs each weighing 300-400 g. The abdominal hair of the guinea pigs was shaved to form a circle having a diameter of 2 cm, where a test sample was applied. On the following day, shaving and another application of the sample were carried out and this was repeated every day (total of five days). On the fifth day, the guinea pigs were evaluated.

Averages of the evaluations of the five guinea pigs which constituted the test group are shown in Table 2.

| Evaluation standard: | |
|---|---|
| Same degree of redness as comparative product was observed | C |
| Less degree of redness than that observed with comparative product | B |
| Slight degree of redness was observed | A |

TABLE 2

| | (% by weight) | | |
|---|---|---|---|
| | Invention products | | Comparative Product |
| Components | 4 | 6 | 5 |
| L-cysteine | 6.0 | 6.0 | 6.0 |
| Ammonium thioglycolate | 1.0 | 1.0 | 1.0 |
| EDTA.4Na | 0.5 | 0.5 | 0.5 |
| Monoethanolamine | ← Suitable amount*1 → | | |
| Sorbitol | 5.0 | 10.0 | — |
| Water | ← Balance → | | |
| Mildness to the skin | B | A | C |

*1 Amount required to adjust pH to 9.0

EXAMPLE 3

Using the compositions shown in Table 3, the presence or absence of flaking was determined. 50 microliters of each of the compositions were dropped on a transparent glass plate and allowed to dry. The conspicuousness of crystals was observed by the naked eye on a backscreen of black color. The results are shown in Table 3.

| Evaluation: Conspicuousness of crystals: | |
| --- | --- |
| Slight: | A |
| Moderate: | B |
| Very conspicuous: | C |

TABLE 3

| | (% by weight) | | | | |
| --- | --- | --- | --- | --- | --- |
| | Invention products | | | | Comparative Product |
| Components | 1 | 2 | 3 | 4 | 5 |
| L-cysteine | 6.0 | 6.0 | 6.0 | 6.0 | 6.0 |
| Ammonium thioglycolate | 1.0 | 1.0 | 1.0 | 1.0 | 1.0 |
| EDTA.4Na | 0.5 | 0.5 | 0.5 | 0.5 | 0.5 |
| Monoethanolamine | ← Suitable amount*[1] → | | | | |
| Inositol | 5.0 | — | — | — | — |
| Saccharose | — | 5.0 | — | — | — |
| Sodium gluconate | — | — | 5.0 | — | — |
| Sorbitol | — | — | — | 5.0 | — |
| Water | ← Balance → | | | | |
| Conspicuousness of crystals | B | A | A | B | C |

*[1]Amount required to adjust pH to 9.0

Having now fully described the invention, it will be apparent to one of ordinary skill in the art that many changes and modifications can be made thereto without departing from the spirit or scope of the invention as set forth herein.

What is claimed is:

1. A hair treatment composition, which comprises:
   (A) 3 to 10% by weight, calculated as a cysteine, of cysteine or a salt thereof, and
   (B) a monosaccharide having 4 to 10 carbon atoms and having no aldehyde or ketone group, $C_4$–$C_{10}$ straight chain or cyclic polyhydric alcohols, condensation products of two or three of said monosaccharides or polyhydric alcohols, saccharides which are produced by condensation of two or three monosaccharides having 4 to 10 carbon atoms and also having an aldehyde group or a ketone group, with the aldehyde or ketone group being eliminated during the course of the condensation process, the proportion by weight of (B)/(A) being less than 3.

2. The hair treatment composition according to claim 1 wherein said component (B) is selected from the group consisting of aldonic acids, saccharic acids, sugar alcohols, condensed saccharides and cyclic polyhydric alcohols.

3. The hair treatment composition according to claim 1, wherein said component (B) is selected from the group consisting of sorbitol, mannitol, maltitol, xylitol, saccharose, gluconic acid or its salts and inositol.

4. The hair treatment composition according to claim 1, wherein the amount of said component (B) is 0.5 to 20% by weight based upon the total composition.

5. The hair treatment according to claim 1, wherein said hair treatment composition is a permanent wave agent or a set lotion.

6. The hair treatment composition according to claim 5, which further comprises a chelating agent and a base.

* * * * *